(12) United States Patent
Neuberger et al.

(10) Patent No.: US 7,177,487 B2
(45) Date of Patent: Feb. 13, 2007

(54) DETERMINATION OF PARTICLE SIZE BY IMAGE ANALYSIS

(75) Inventors: Damian Neuberger, Glenview, IL (US); Joseph Chung Tak Wong, Gurnee, IL (US)

(73) Assignee: Baxter International Inc., Deerfield, IL (US)

( * ) Notice: Subject to any disclaimer, the term of this patent is extended or adjusted under 35 U.S.C. 154(b) by 837 days.

(21) Appl. No.: 10/419,612

(22) Filed: Apr. 21, 2003

(65) Prior Publication Data
US 2004/0208352 A1   Oct. 21, 2004

(51) Int. Cl.
*G06K 9/32* (2006.01)
(52) U.S. Cl. .............. 382/296; 399/130; 430/31; 356/335; 356/237.3; 428/206
(58) Field of Classification Search ........... 430/31, 430/45, 110.4, 108.21, 108.6, 106.2, 528, 430/109; 382/296; 428/195.1, 206; 399/130, 399/252, 277; 356/335, 237.3
See application file for complete search history.

(56) References Cited

U.S. PATENT DOCUMENTS

| | | | | |
|---|---|---|---|---|
| 5,004,668 | A | * | 4/1991 | Namiki et al. ............ 430/256 |
| 5,378,917 | A | * | 1/1995 | Chalupka et al. ...... 250/492.21 |
| 5,590,059 | A | * | 12/1996 | Schier .................... 702/151 |
| 5,721,433 | A | | 2/1998 | Kosaka |
| 5,812,248 | A | * | 9/1998 | Ruck et al. ............... 356/28 |
| 6,214,560 | B1 | * | 4/2001 | Yguerabide et al. ........ 435/7.1 |
| 6,650,409 | B1 | * | 11/2003 | Noguchi et al. ........ 356/237.3 |
| 6,697,517 | B1 | * | 2/2004 | Hunter .................... 382/149 |
| 7,015,046 | B2 | * | 3/2006 | Wohlstadter et al. ....... 436/172 |

(Continued)

FOREIGN PATENT DOCUMENTS

DE   10125277 A1   9/2002

OTHER PUBLICATIONS

Archambault, Marie-Claude, Grant, Jon, and Hatcher, Annamarie, "The small volume particle microsampler (SVPM): a new approach to particle size distribution and composition".

(Continued)

*Primary Examiner*—Sheela Chawan
(74) *Attorney, Agent, or Firm*—Michael C. Mayo; Raymond M. Mehler

(57) ABSTRACT

The present invention provides a method for determining a particle size. The process includes the steps of: (i) positioning a particle on a flat surface; (ii) recording a digital image of the particle on the flat surface wherein the digital image is recorded with an image plane parallel to the flat surface and the digital image of the particle includes a digital background of the flat surface; (iii) removing the digital background image of the flat surface to obtain an isolated digital image of the particle; (iv) determining a surface area (A) of the particle from the isolated digital image of the particle; (v) tilting the particle at an angle (θ) with respect to the image plane to expose an edge of the particle; (vi) measuring a measured thickness ($T_m$) of the particle; (vii) determining a calculated actual thickness (T) of the particle by the equation $T=T_m/\sine \theta$; (viii) determining a particle volume (V) of the particle by the equation $V=A*T$; and (ix) determining an equivalent spherical particle size diameter (D) of the particle by the equation $D=2*\sqrt[3]{(3/4)(1/\pi)(V)}$.

29 Claims, 9 Drawing Sheets

U.S. PATENT DOCUMENTS

| | | |
|---|---|---|
| 7,033,781 B1 * | 4/2006 | Short ................... 435/69.1 |
| 2002/0127278 A1 | 9/2002 | Kipp et al. |
| 2002/0168402 A1 | 11/2002 | Kipp et al. |
| 2002/0176935 A1 | 11/2002 | Kipp et al. |
| 2003/0031719 A1 | 2/2003 | Kipp et al. |
| 2003/0044433 A1 | 3/2003 | Werling et al. |
| 2003/0059472 A1 | 3/2003 | Brynjelsen et al. |
| 2003/0072807 A1 | 4/2003 | Wong et al. |
| 2003/0077329 A1 | 4/2003 | Kipp et al. |
| 2003/0096013 A1 | 5/2003 | Werling et al. |
| 2003/0100568 A1 | 5/2003 | Werling et al. |

OTHER PUBLICATIONS

Allen et al., "Critical Evaluation of Acute Cardiopulmonary Toxicity of Microspheres", Journal of Nuclear Medicine, vol. 19, pp. 1204-1208, 1987.

Davis et al., "Pulmonary Perfusion Imaging: Acute Toxicity and Safety Factors as a Function of Particle Size", Journal of Nuclear Medicine, vol. 19, pp. 1209-1213, 1987.

Shroeder et al., "Physiological Effects of Subvisible Microspheres Administered Intravenously to Beagle Dogs", Journal of Pharmaceutical Sciences, vol. 67, No. 4, Apr. 1978, pp. 508-512.

Yokel et al., "Acute Toxicity of Latex Microspheres", Toxicology Letters, vol. 9 (1981), pp. 165-170.

* cited by examiner

DETERMINATION OF PARTICLE SIZE BY IMAGE ANALYSIS

CROSS-REFERENCE TO RELATED APPLICATIONS

Not applicable.

FEDERALLY SPONSORED RESEARCH OR DEVELOPMENT

Not applicable.

BACKGROUND OF THE INVENTION

1. Technical Field

The present invention is concerned with methods to determine particle size by image analysis, particularly by scanning electron photomicrographs.

2. Background Art

There are an ever-increasing number of organic compounds being formulated for therapeutic or diagnostic effects that are poorly soluble or insoluble in aqueous solutions. Such drugs provide challenges to delivering them by the administrative routes detailed above. Compounds that are insoluble in water can have significant benefits when formulated as a stable suspension of sub-micron particles. Accurate control of particle size is essential for safe and efficacious use of these formulations. Particles must be less than seven microns in diameter to safely pass through capillaries without causing emboli (Allen et al., 1987; Davis and Taube, 1978; Schroeder et al., 1978; Yokel et al., 1981). One solution to this problem is the production of small particles of the insoluble drug candidate and the creation of a microparticulate or nanoparticulate suspension. In this way, drugs that were previously unable to be formulated in an aqueous based system can be made suitable for intravenous administration. Suitability for intravenous administration includes small particle size (<7 μm), low toxicity (as from toxic formulation components or residual solvents), and bioavailability of the drug particles after administration.

Preparations of small particles of water insoluble drugs may also be suitable for oral, pulmonary, topical, ophthalmic, nasal, buccal, rectal, vaginal, transdermal administration, or other routes of administration. The small size of the particles improves the dissolution rate of the drug, and hence improving its bioavailability and potentially its toxicity profiles. When administered by these routes, it may be desirable to have particle size in the range of 5 to 100 μm, depending on the route of administration, formulation, solubility, and bioavailability of the drug. For example, for intravenous administration, it is desirable to have a particle size of less than about 7 μm. For pulmonary administration, the particles are preferably less than about 10 μm in size.

Determination of the size of these particles has been routinely performed by image analysis using optical light microscopy. However, performing accurate and precise analysis of small particles, especially those below one micron, becomes difficult due to the limited number of pixels available for each particle and also the practical (and theoretical) limits of resolution of the light microscope. Moreover, image analysis of particles approximately less than or equal to 1 μm in suspension is not feasible due to the Brownian motion of the particles and their constant motion in X, Y and Z directions on a standard slide preparation.

Image analysis of particles can be performed by a variety of methods and algorithms. Typically, a particle is positioned onto a depth filter and the image of the particle is isolated using a threshold algorithm to separate the image of the particle from the image of the background. In the case of particles less than 1 μm, a variety of problems occur. For example, depth filters do not present all the particles (some are embedded into the filter matrix) nor do they present all the particles normal to the optical axis. While nuclear track etched membrane filters present a smooth, flat surface perforated by more or less circular holes, these membranes do not provide for sufficient contrast between the particles and the membrane surface. Additionally, the holes of the nuclear track etched membrane filter may be detected as particles, thus causing another source of error.

The present invention discloses a method to determine particle size using image analysis. The method is particularly suitable for small particles such as those that are less than 1 μm in size.

SUMMARY OF THE INVENTION

The present invention provides a method for determining a particle size. The process includes the steps of: (i) positioning a particle on a flat surface; (ii) recording a digital image of the particle on the flat surface wherein the digital image is recorded with an image plane parallel to the flat surface and the digital image of the particle includes a digital background of the flat surface; (iii) removing the digital background image of the flat surface to obtain an isolated digital image of the particle; (iv) determining a surface area (A) of the particle from the isolated digital image of the particle; (v) tilting the particle at a known angle ($\theta$) with respect to the image plane to expose an edge of the particle; (vi) measuring a measured thickness ($T_m$) of the particle; (vii) determining a calculated actual thickness (T) of the particle by the equation $T = T_m / \sin \theta$; (viii) determining a particle volume (V) of the particle by the equation $V = A * T$; and (ix) determining an equivalent spherical particle size diameter (D) of the particle by the equation $D = 2 * \sqrt[3]{(3/4)(1/\pi)(V)}$.

These and other aspects and attributes of the present invention will be discussed with reference to the following drawings and accompanying specification.

DETAILED DESCRIPTION OF THE INVENTION

Figure 1:
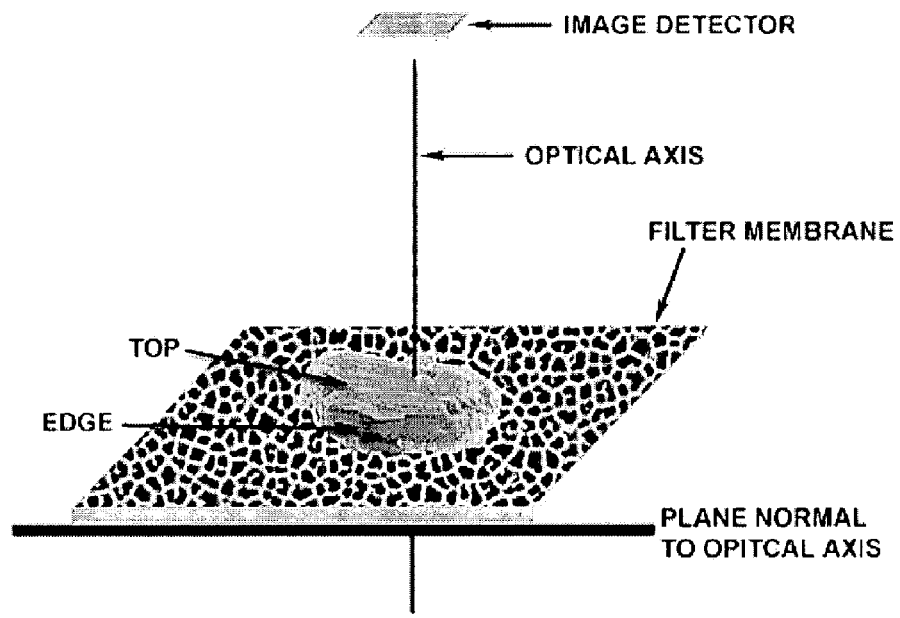
FIG. 1 is a schematic diagram showing the parallel alignment of the image detector, optical axis, particle, and membrane surface.

While this invention is susceptible of embodiment in many different forms, there is shown in the drawing, and will be described herein in detail, specific embodiments thereof with the understanding that the present disclosure is to be considered as an exemplification of the principles of the invention and is not intended to limit the invention to the specific embodiments illustrated.

The present invention provides a method for determining a particle size. The process includes the steps of: (i) positioning a particle on a flat surface; (ii) recording a digital image of the particle on the flat surface wherein the digital image is recorded with an image plane parallel to the flat surface and the digital image of the particle includes a digital background of the flat surface; (iii) removing the digital background image of the flat surface to obtain an isolated digital image of the particle; (iv) determining a surface area (A) of the particle from the isolated digital image of the particle; (v) tilting the particle at a known angle ($\theta$) with respect to the image plane to expose an edge of the particle; (vi) measuring a measured thickness ($T_m$) of the particle; (vii) determining a calculated actual thickness (T) of the particle by the equation $T = T_m / \sine \theta$; (viii) determining a particle volume (V) of the particle by the equation $V = A*T$; and (ix) determining an equivalent spherical particle size diameter (D) of the particle by the equation $D = 2 * \sqrt[3]{(3/4)(1/\pi)(V)}$. It should be appreciated that this method may be repeated with more than one particle on the surface to obtain an average value of the particle population size or a particle population size range.

The particle for use in the present invention may be a crystalline particle or an amorphous particle. The particles most suitable for the present invention are generally small, preferably less than about 1 micron in size. In other preferred embodiments, the particle sizes are greater than about 350 nm, from 250 nm to 350 nm, greater than about 210 nm, or any range or combination of ranges therein.

The particles of the present invention can be prepared by any of the methods known in the art. The methods include, but are not limited to, microprecipitation methods or emulsion methods. Examples of these methods are disclosed in co-pending and commonly assigned U.S. patent applications Ser. Nos. 60/258,160; 09/874,799; 09/874,637; 09/874,499; 09/964,273; 10/035,821, 60/347,548; 10/021,692; 10/183,035; 10/213,352; 10/246,802; 10/270,268; 10/270,267, and 10/390,333 which are incorporated by reference herein and are made a part hereof.

The particle may be an organic or an inorganic compound. The compound might be a pharmaceutically active compound, which can be selected from therapeutic agents, diagnostic agents, cosmetics, nutritional supplements, and pesticides.

The therapeutic agents can be selected from a variety of known pharmaceuticals such as, but are not limited to: analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, anorexiants, antacids, antidiarrheals, antidotes, antifolics, antipyretics, antirheumatic agents, psychotherapeutic agents, neural blocking agents, anti-inflammatory agents, antihelmintics, anti-arrhythmic agents, antibiotics, anticoagulants, antidepressants, antidiabetic agents, antiepileptics, antifungals, antihistamines, antihypertensive agents, antimuscarinic agents, antimycobacterial agents, antimalarials, antiseptics, antineoplastic agents, antiprotozoal agents, immunosuppressants, immunostimulants, antithyroid agents, antiviral agents, anxiolytic sedatives, astringents, beta-adrenoceptor blocking agents, contrast media, corticosteroids, cough suppressants, diagnostic agents, diagnostic imaging agents, diuretics, dopaminergics, hemostatics, hematological agents, hemoglobin modifiers, hormones, hypnotics, immunological agents, antihyperlipidemic and other lipid regulating agents, muscarinics, muscle relaxants, parasympathomimetics, parathyroid calcitonin, prostaglandins, radio-pharmaceuticals, sedatives, sex hormones, anti-allergic agents, stimulants, sympathomimetics, thyroid agents, vasodilators, vaccines, vitamins, and xanthines. Antineoplastic, or anticancer agents, include but are not limited to paclitaxel and derivative compounds, and other antineoplastics selected from the group consisting of alkaloids, antimetabolites, enzyme inhibitors, alkylating agents and antibiotics. The therapeutic agent can also be a biologic, which includes but is not limited to proteins, polypeptides, carbohydrates, polynucleotides, and nucleic acids. The protein can be an antibody, which can be polyclonal or monoclonal.

Diagnostic agents include the x-ray imaging agents and contrast media. Examples of x-ray imaging agents include WIN-8883 (ethyl 3,5-diacetamido-2,4,6-triiodobenzoate) also known as the ethyl ester of diatrazoic acid (EEDA), WIN 67722, i.e., (6-ethoxy-6-oxohexyl-3,5-bis(acetamido)-2,4,6-triiodobenzoate; ethyl-2-(3,5-bis(acetamido)-2,4,6-triiodobenzoyloxy) butyrate (WIN 16318); ethyl diatrizoxyacetate (WIN 12901); ethyl 2-(3,5-bis(acetamido)-2,4,6- triiodobenzoyloxy) propionate (WIN 16923); N-ethyl 2-(3,5-bis(acetamido)-2,4,6-triiodobenzoyloxy acetamide (WIN 65312); isopropyl 2-(3,5-bis(acetamido)-2,4,6-triiodobenzoyloxy) acetamide (WIN 12855); diethyl 2-(3,5-bis(acetamido)-2,4,6-triiodobenzoyloxy) malonate (WIN 67721); ethyl 2-(3,5-bis(acetamido)-2,4,6-triiodobenzoyloxy) phenylacetate (WIN 67585); propanedioic acid, [[3,5-bis(acetylamino)-2,4,5-triodobenzoyl]oxy]bis(1-methyl)ester (WIN 68165); and benzoic acid, 3,5-bis(acetylamino)-2,4,6-triodo-4-(ethyl-3-ethoxy-2-butenoate) ester (WIN 68209). Preferred contrast agents include those that are expected to disintegrate relatively rapidly under physiological conditions, thus minimizing any particle associated inflammatory response. Disintegration may result from enzymatic hydrolysis, solubilization of carboxylic acids at physiological pH, or other mechanisms. Thus, poorly soluble iodinated carboxylic acids such as iodipamide, diatrizoic acid, and metrizoic acid, along with hydrolytically labile iodinated species such as WIN 67721, WIN 12901, WIN 68165, and WIN 68209 or others may be preferred.

Other contrast media include, but are not limited to, particulate preparations of magnetic resonance imaging aids such as gadolinium chelates, or other paramagnetic contrast agents. Examples of such compounds are gadopentetate dimeglumine (Magnevist®) and gadoteridol (Prohance®).

A description of these classes of therapeutic agents and diagnostic agents and a listing of species within each class can be found in Martindale, The Extra Pharmacopoeia, Twenty-ninth Edition, The Pharmaceutical Press, London, 1989 which is incorporated herein by reference and made a part hereof. The therapeutic agents and diagnostic agents are commercially available and/or can be prepared by techniques known in the art.

A cosmetic agent is any active ingredient capable of having a cosmetic activity. Examples of these active ingredients can be, inter alia, emollients, humectants, free radical-inhibiting agents, anti-inflammatories, vitamins, depigmenting agents, anti-acne agents, antiseborrhoeics, keratolytics, slimming agents, skin coloring agents and sunscreen agents, and in particular linoleic acid, retinol, retinoic acid, ascorbic acid alkyl esters, polyunsaturated fatty acids, nicotinic esters, tocopherol nicotinate, unsaponifiables of rice, soybean or shea, ceramides, hydroxy acids such as glycolic acid, selenium derivatives, antioxidants, beta-carotene, gamma-orizanol and stearyl glycerate. The cosmetics are commercially available and/or can be prepared by techniques known in the art.

Examples of nutritional supplements contemplated for use in the practice of the present invention include, but are not limited to, proteins, carbohydrates, water-soluble vitamins (e.g., vitamin C, B-complex vitamins, and the like), fat-soluble vitamins (e.g., vitamins A, D, E, K, and the like), and herbal extracts. The nutritional supplements are commercially available and/or can be prepared by techniques known in the art.

The term pesticide is understood to encompass herbicides, insecticides, acaricides, nematicides, ectoparasiticides and fungicides. Examples of compound classes to which the pesticide in the present invention may belong include ureas, triazines, triazoles, carbamates, phosphoric acid esters, dinitroanilines, morpholines, acylalanines, pyrethroids, benzilic acid esters, diphenylethers and polycyclic halogenated hydrocarbons. Specific examples of pesticides in each of these classes are listed in Pesticide Manual, 9th Edition, British Crop Protection Council. The pesticides are commercially available and/or can be prepared by techniques known in the art.

The particle size determination of the present invention begins with positioning one or more particles on a flat surface. In a preferred embodiment, the step of positioning the particle on the flat surface is by providing a dilute suspension of one or more particles in a liquid medium and filtering the suspension onto a retention filter. The liquid medium can be an aqueous medium or a non-aqueous medium compatible to the filter used. The filtered particles are preferably separated from each other on the filter with no overlap or little or no touching of the particles on the filter. In a preferred embodiment, the flat surface is a membrane filter. In one embodiment, the membrane filter is an anodized aluminum membrane filter with a smooth flat surface, such as an Anodisc™ membrane filter. In another embodiment, the membrane filter is a nuclear track-etched membrane filter with a smooth flat surface. In yet another preferred embodiment, the membrane filter is a retention rated filter wherein the size of the particles to be analyzed is greater than the retention rating. For example, if the filter is a 0.2 μm retention rated membrane filter, then the particle size is greater than 0.2 μm.

With the particle on the flat surface, the image of the particle is digitally recorded. The digital image is recorded from directly above the particle with an image plane parallel to the top surface of the particle (FIG. 1), thus producing an overhead view of the particle on the flat surface. This recorded digital image includes the digital image of the particle as well as the digital image of the background from the flat surface.

The digital image can be recorded by any suitable method, including but not limited to, a scanning electron microscope, an optical microscope, a laser scanning microscope, a confocal microscope or a scanning probe microscope and the like.

In the embodiment in which a scanning electron microscope is used, the microscope is preferably a high resolution field emission, low voltage scanning electron microscope. In one embodiment, the scanning electron microscope has a backscattered detector. In another embodiment, the scanning electron microscope has a multichannel plate detector. In another embodiment, the scanning electron microscope has a secondary electron detector. An example of a suitable scanning electron microscope is a high resolution JEOL 6300F field emission, low voltage scanning electron microscope (FE-LVSEM) using the MCP secondary electron detector, a SEI detector or a BSE detector.

In a preferred embodiment, the digital image of the particle on the flat surface is recorded by a scanning electron microscope by mounting the flat surface to a specimen support. The mounting can be with the use of double sided stick carbon discs. In one embodiment, the flat surface is an anodized aluminum membrane and the particle is placed on the filter by filtering a dilute suspension of the particles through the filter. In this embodiment, the filter (with the retained particles on the filter) is vacuum sputter coated with palladium for 30–45 seconds before recording the digital imager. In an alternative embodiment wherein the dilute suspension is filtered onto the nuclear track-etched PC membrane filter, the membrane filter is pre-coated with gold or palladium prior to filtration and the filter (with the filtered particles) is not vacuum sputter coated. The coating may be performed by vacuum evaporation, vaccum ion-beam sputtering, or vacuum magnetron sputtering of an electron conductive material.

After recording the digital image of the particle including the background from the flat surface, the background image of the flat surface is removed to obtain the isolated, shadow free digital image of the particle. This can be accomplished by applying one or more image analysis or image processing filters using an appropriate value depending on the image brightness to remove the background. In one embodiment, the image analysis or image processing filter removes the digital background image of the surface from the digital image of the particle by a number of pixels. The number of pixels can be a whole number or a fractional number. After removing the digital background image of the surface, the image analysis filter then reduces at least one edge of the digital image of the particle by the same number of pixels which have been removed and adds the same number of pixels back to the reduced edge of the digital image of the particle to produce the isolated digital image of the particle without the background. One example of the image analysis filter is performed by using Adobe Photoshop Software with the commands described in Example 1. Examples of other softwares which can be used to perform image analysis are Metamorph, Image Pro Plus, NIH Image and its derivatives and the like.

In another embodiment, the particle is isolated by using the Lasso tool in Adobe Photoshop. The area selected by the Lasso tool is then Edit→Fill→Contents Use: Black, Blending Mode: Normal, Opacity: 100%. The Select→Inverse is applied and the area outside the particle is Edit→Fill→Contents Use: White, Blending Mode: Normal, Opacity: 100%.

After obtaining the isolated digital image of the particle, the surface area and the surface length of the particle can be determined from the isolated digital image using the Filter→IP Features→Measure All Fovea Pro 2.0 plugin.

In order to measure and determine the thickness of the particle to calculate the particle volume, the flat surface (including the particle) is tilted by a known angle (?) with respect to the image plane to expose an edge of the particle. The tilting is accomplished via an external manual or motorized mechanical tilt mechanism with a tilt angle readout scale. In a preferred embodiment, the particle is tilted at a 45° angle. However any other suitable known angles may be used with the present invention.

Figure 2:
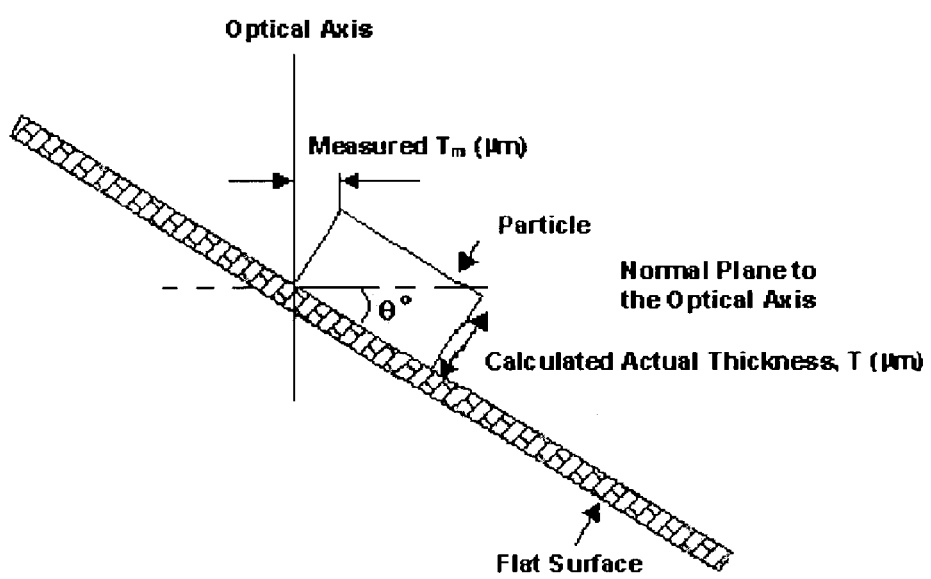
FIG. 2 is a schematic diagram of a tilted particle for measuring and calculating the actual thickness of the particle.

After tilting the particle, a digital image of the exposed edge of the tilted particle on the surface is recorded along the same optical axis as the previous step in which the particle is not tilted. As described above, this digital image includes a digital background image of the surface. It is preferred that this image is recorded at a higher magnification than the magnification used previously to measure the surface area and length of the untilted particle. The width of the exposed edge of the particle from the digital image of the tilted particle is then measured (see FIG. 2). In one embodiment, the width of the edge of the particle is measured with a NIST traceable ruler. In another embodiment, the width of the edge of the tilted particle is measured by image analysis software with a calibrated line measurement feature. It should be appreciated that any other suitable method for measuring the edge of the particle from the digital image of the titled particle may be implemented with the present invention.

Once the width of the exposed edge of the particle is measured (the measured thickness, or $T_m$), a calculated actual thickness (T) of the particle can be determined manually, automatically or semi-automatically by correcting the tilt angle measurement of the thickness using the following formulas.

$$\text{Sine } \theta = \text{measured thickness } (T_m)/\text{actual thickness } (T)$$

$$T = T_m/\text{sine } \theta$$

The volume of the particle is calculated using the formula $$\text{Volume } (V) = \text{area } (A) * \text{actual thickness } (T)$$

wherein the area (A) is the surface area of the particle. Since the volume of an equivalent sphere is represented by the equation $$V = (4/3) * \pi * R^3$$

where R is the radius of the equivalent sphere of the particle, and R can be calculated by the solving the above equation:

$$R^3 = (3/4)(1/\pi)(V) \text{ or}$$

$$R = \sqrt[3]{(3/4)(1/\pi)(V)}.$$

With the determined radius for the equivalent sphere of each particle, the equivalent spherical particle size diameter (D) of each selected particle is determined with the equation $$D = 2R \text{ or } D = 2 * \sqrt[3]{(3/4)(1/\pi)(V)}.$$

EXAMPLE 1

Determination of the Size of Itraconazole Particles

Figure 3:
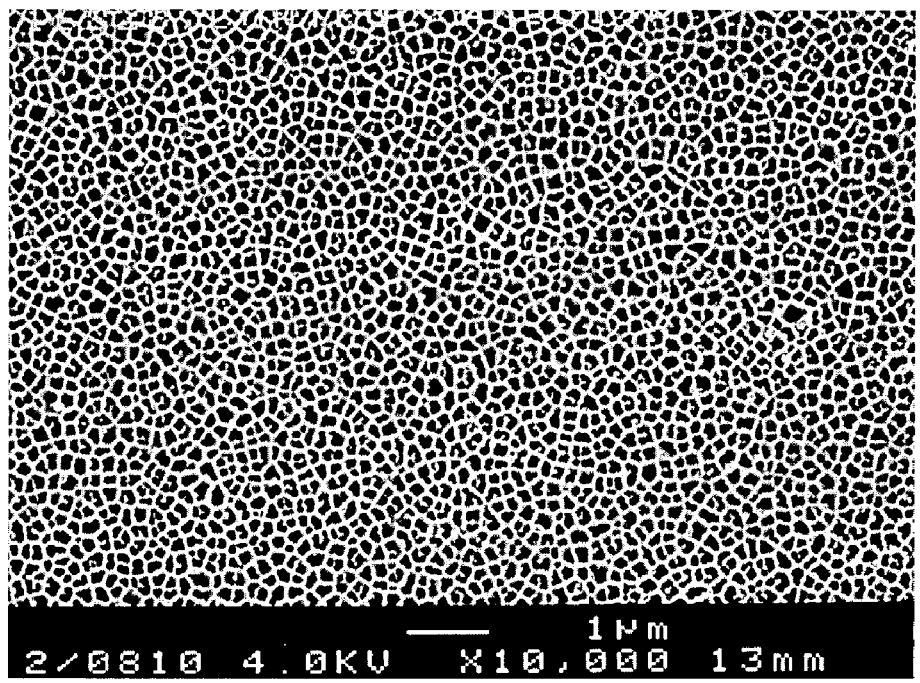
FIG. 3 is a scanning electron photomicrograph of a blank anodized aluminum membrane filter recorded at 10,000× magnification.
Figure 4:
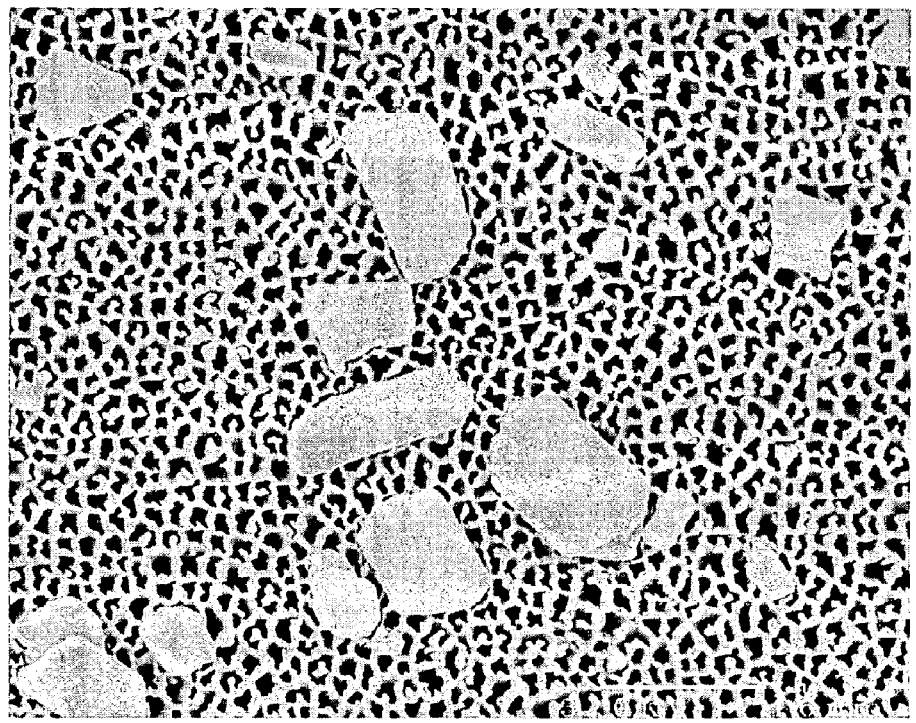
FIG. 4 is a scanning electron photomicrograph of a population of itraconazole particles of Example 1 on an anodized aluminum membrane filter recorded at 10,000× magnification (scale bar=1 μm)

A dilute suspension of itraconazole particles was prepared and filtered onto a blank 0.2 μm retention rated anodized aluminum membrane filter. The filter with the retained particles was then mounted onto an aluminum scanning electron microscope specimen support using double sided carbon discs and vacuum sputter coated with palladium for 30 to 45 seconds. The membrane filter was then examined by a high resolution JEOL 6300F field emission, low voltage scanning electron microscope (FE-LVSEM) using the MCP secondary electron detector. Digital images of particles on the filter (which included a digital image of the itraconazole particles and a digital image of background from the membrane filter) were recorded from directly above the membrane filter with an image plane parallel to the surface of the filter and the particles. FIG. 3 shows a scanning electron photomicrograph of the blank anodized aluminum membrane filter without the particles recorded at 10,000× magnification. FIG. 4 shows scanning electron photomicrograph of a population of itraconazole particles filtered onto the anodized aluminum membrane filter recorded at 10,000× magnification. The digital image of FIG. 4 includes the digital image of the particle and the digital image of the background from the filter.

An image analysis filter was then performed on the digital image to remove the background image of the membrane filter in order to obtain the isolated, shadow free image of the population of itraconazole particles. The image analysis filter was performed using Adobe Photoshop 7.0, (Adobe Systems, Inc., San Jose, Calif.) and Fovea 2.0 (Reindeer Graphics, Inc., Asheville, N.C.) using the following software commands:

1. OPEN <file name>
2. FILTER→OTHER→MIMIMUM (RADIUS 4 or other appropriate value)
3. REPEAT STEP 2 AS NEEDED
4. FILTER→NOISE→MEDIAN (RADIUS 4 or other appropriate value)
5. FILTER→OTHER→MAXIMUM (RADIUS 4 or other appropriate value)
6. REPEAT STEP 5 AS NEEDED
7. IMAGE→ADJUSTMENTS→THRESHOLD (VALUE SET BETWEEN 60 AND 160 DEPENDING ON IMAGE BRIGHTNESS; other appropriate values may be used depending on the image)

8. INVERT
9. FILTER→IP FEATURES→MEASURE ALL
10. SAVE AS <file name>.

Figure 5:
FIG. 5 is the population of Itraconazole drug particles on the anodized aluminum membrane filter isolated after image analysis; letters refer to particle numbers in Table 1.

FIG. 5 illustrates a scanning electron photomicrograph of the population of itraconazole particles isolated after image analysis recorded at 10,000× magnification; the alphabet characters refer to the Particle Numbers in Table 1. The surface areas of the particles and other measured values of the particles were then determined from the isolated digital image of the population of particles and are summarized in Table 1.

TABLE 1

Surface Areas and Lengths of Isolated Particles

| Particle Number | Area ($\mu m^2$) | Length ($\mu m$) |
|---|---|---|
| A | 0.079 | 0.434 |
| B | 0.243 | 0.654 |
| C | 0.045 | 0.311 |
| D | 0.164 | 0.669 |
| E | 0.567 | 1.163 |
| F | 0.202 | 0.626 |
| G | 0.031 | 0.252 |
| H | 0.286 | 0.745 |
| I | 0.477 | 1.252 |
| J | 0.029 | 0.217 |
| K | 0.710 | 1.249 |
| L | 0.463 | 0.907 |
| M | 0.076 | 0.423 |
| N | 0.073 | 0.390 |
| O | 0.185 | 0.637 |
| P | 0.154 | 0.528 |
| Q | 0.023 | 0.197 |
| Average | 0.224 | 0.627 |
| Standard Deviation | 0.210 | 0.344 |

EXAMPLE 2

Determination of the Volume of Itraconazole Particles

Figure 6:
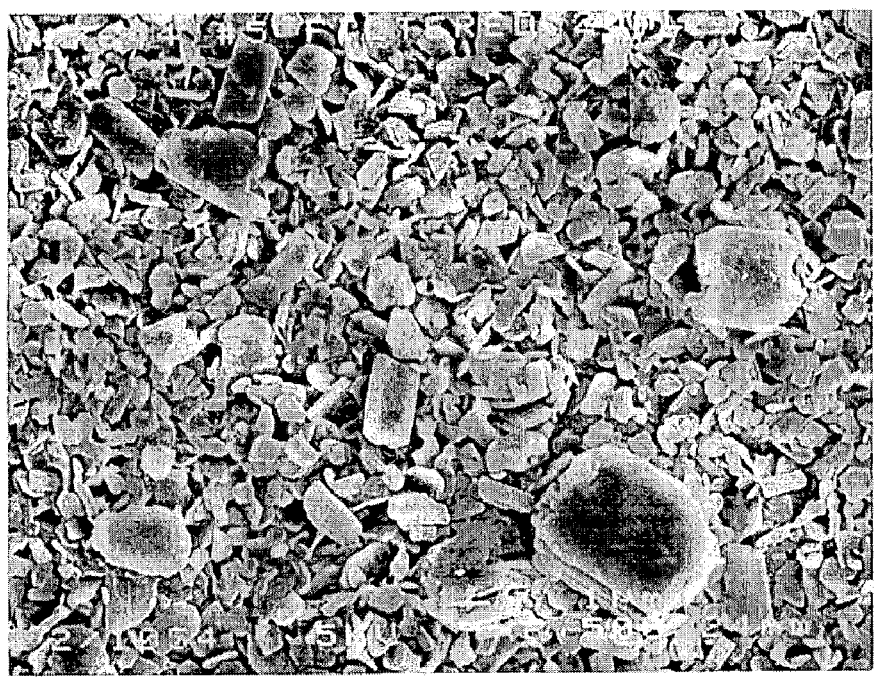
FIG. 6 is a scanning electron photomicrograph of the population of the larger itraconazole particles of Example 2 on the anodized aluminum membrane filter.

A suspension of itraconazole particles of higher concentration than Example 1 was prepared and filtered onto a blank 0.2 μm retention rated anodized aluminum membrane filter. FIG. 6 shows the retained particles on the filter membrane. The filter with the retained particles was then mounted onto an aluminum scanning electron microscope specimen support using double sided carbon discs and vacuum sputter coated with palladium for 30 to 45 seconds. The membrane filter was then examined by a high resolution JEOL 6300F field emission, low voltage scanning electron microscope (FE-LVSEM) using the MCP secondary electron detector. Digital images of particles on the filter (which included a digital image of the itraconazole particles and a digital image of background from the membrane filter) were recorded from directly above the membrane filter with an image plane parallel to the surface of the particle selected for measurement. FIG. 1 shows a diagram of the digital image plane parallel to the particle surface and the membrane surface.

Figure 7:
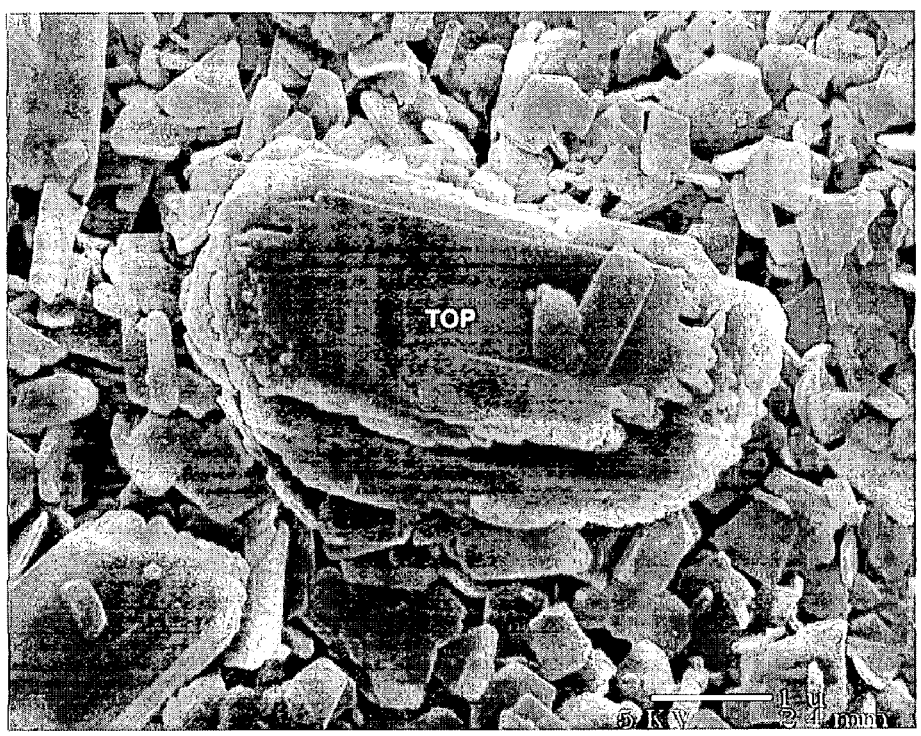
FIG. 7 is a scanning electron photomicrograph of selected particle #1 from the population of itraconazole particles of Example 2 shown normal to the optical axis and recorded at 15,000× magnification.
Figure 8:
FIG. 8 is selected particle #1 from the population of Itraconazole particles of Example 2 isolated after image analysis.
Figure 9:
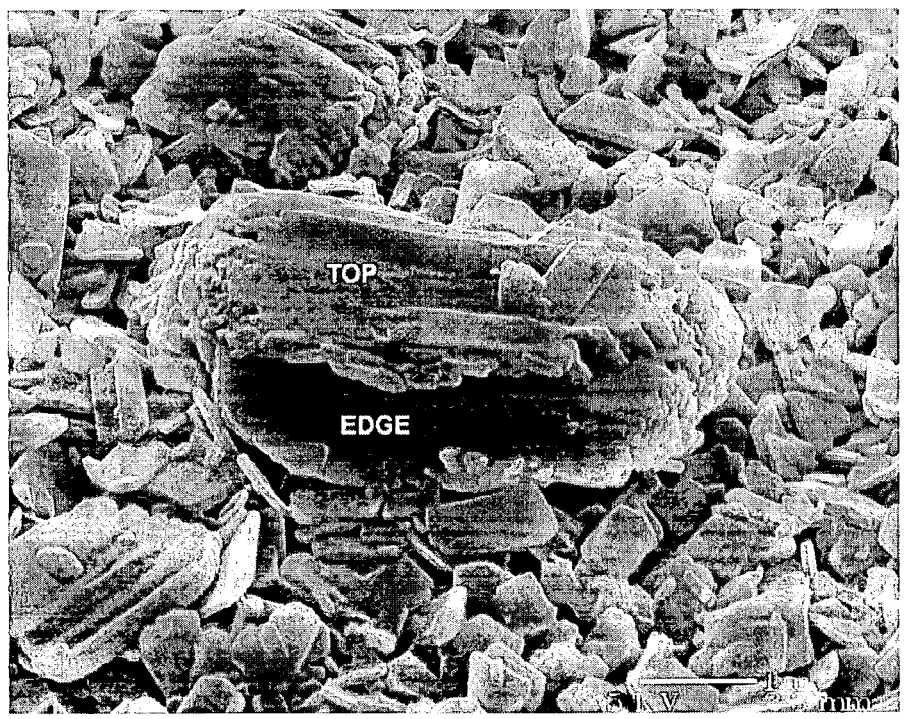
FIG. 9 is a scanning electron photomicrograph of selected particle #1 from the population of itraconazole particles of Example 2 shown tilted 45° to the normal plane.
Figure 10:
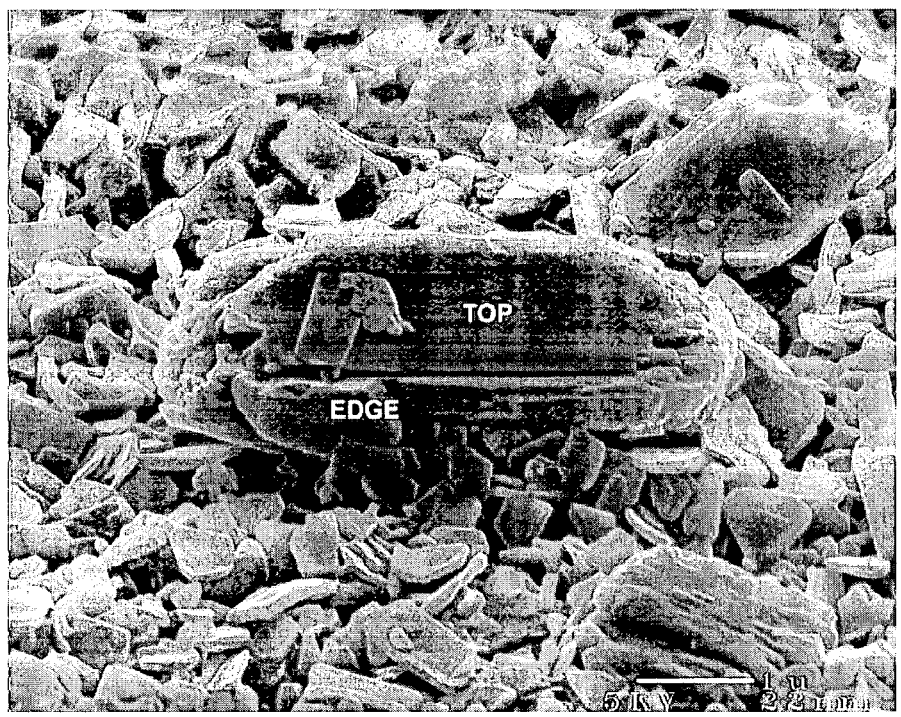
FIG. 10 is a scanning electron photomicrograph of selected particle #1 from the population of itraconazole particles of Example 2 shown rotated 180° and tilted 45° to the normal plane.
Figure 11:
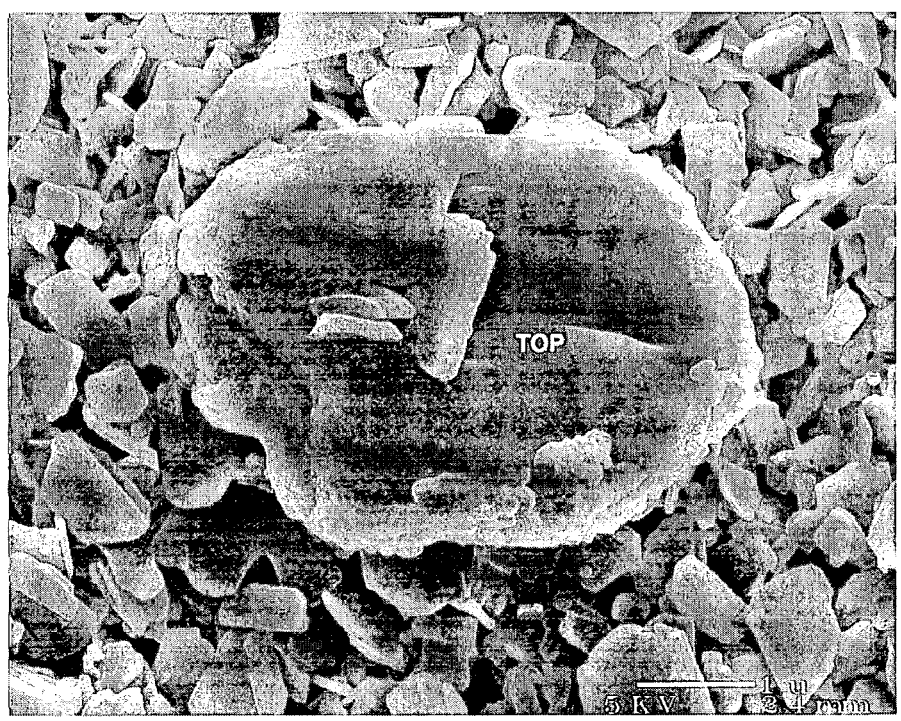
FIG. 11 is a scanning electron photomicrograph of selected particle #2 from the population of itraconazole particles of Example 2 shown normal to the optical axis and recorded at 15,000× magnification.
Figure 12:
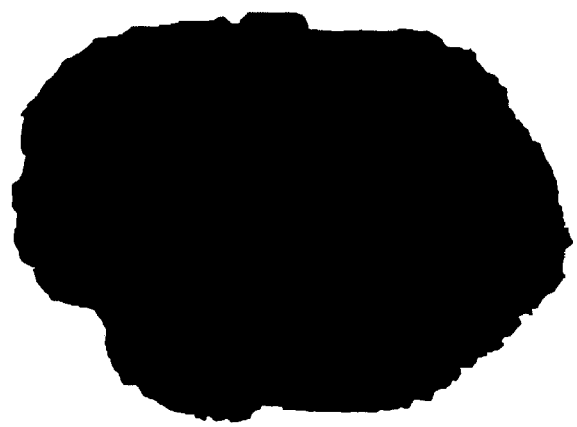
FIG. 12 is selected particle #2 from the population of Itraconazole particles of example 2 isolated after image analysis.
Figure 13:
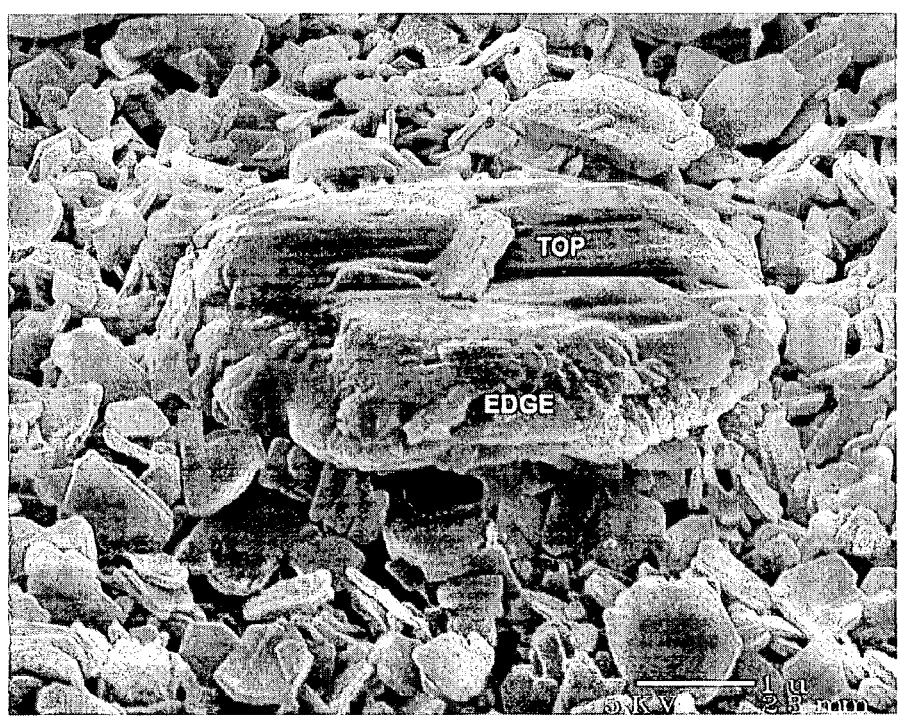
FIG. 13 is a scanning electron photomicrograph of selected particle #2 from the population of itraconazole particles of Example 2 shown tilted 45° to the normal plane.
Figure 14:
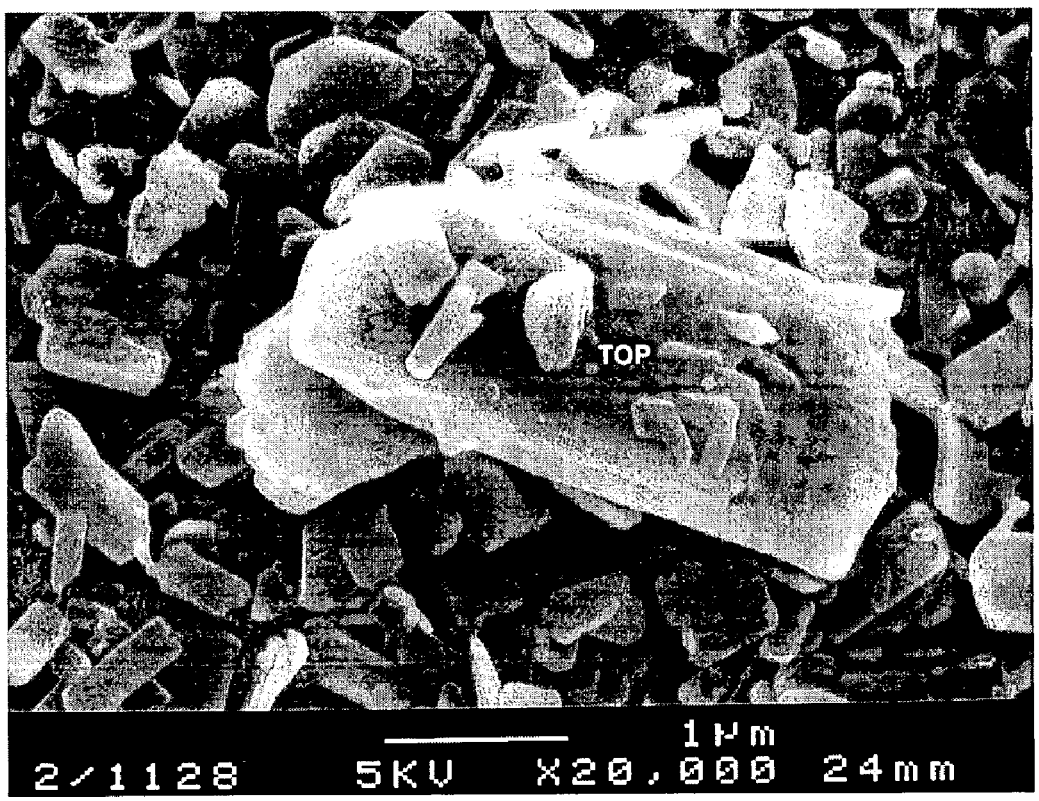
FIG. 14 is a scanning electron photomicrograph of selected particle #3 from the population of itraconazole particles of Example 1 shown normal to the optical axis and recorded at 20,000× magnification.
Figure 15:
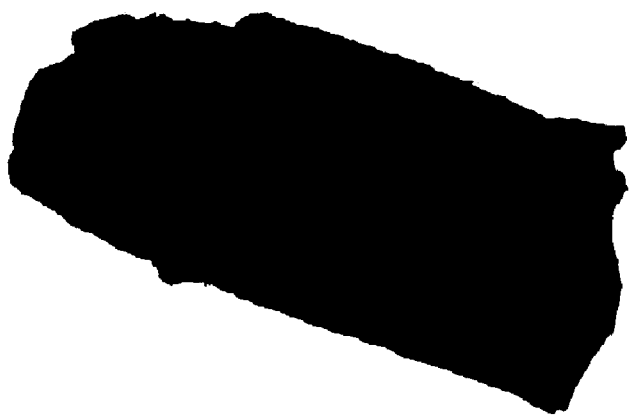
FIG. 15 is selected particle #3 from the population of Itraconazole particles of example 2 isolated after image analysis; and, FIG. 16 is a scanning electron photomicrograph of selected particle #3 from the population of itraconazole particles of Example 2 shown tilted 45° to the normal plane.
Figure 16:
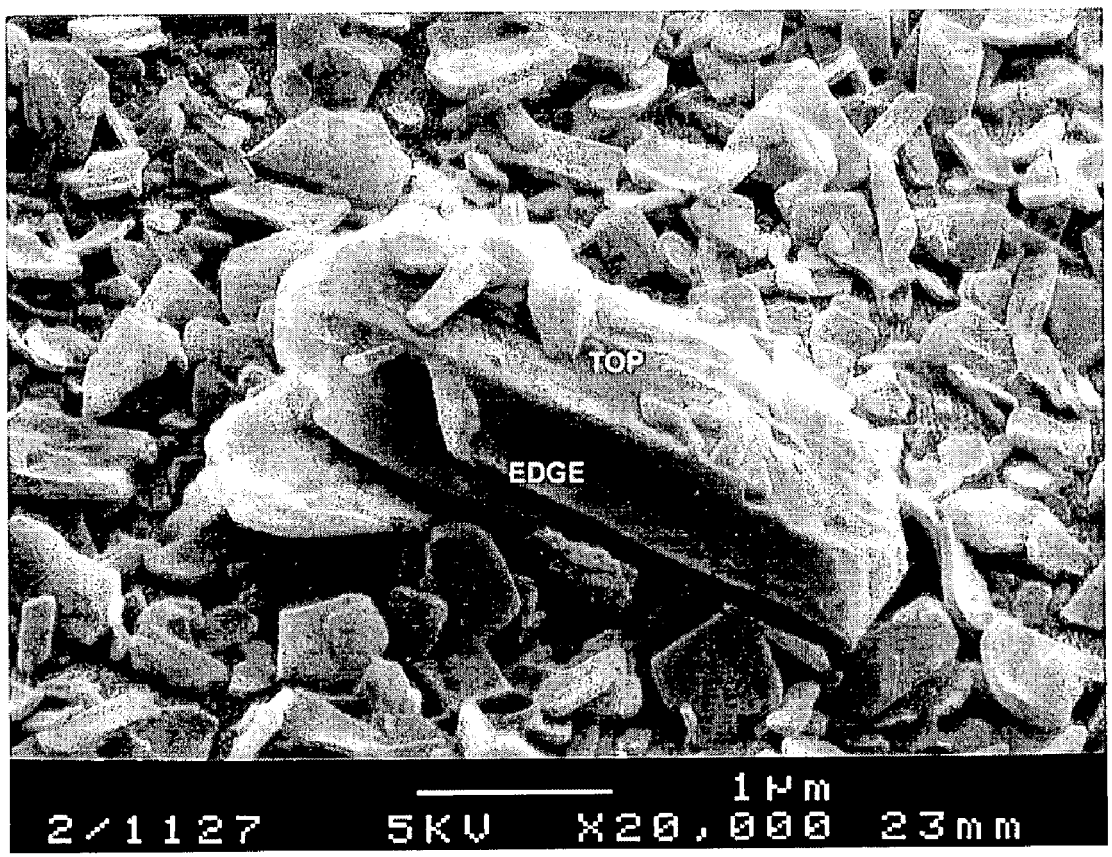

Three particles from the population of particles were selected (particles #1, 2 and 3) for further examination for determining their equivalent sphere volumes and equivalent sphere diameters. These particles were examined under greater magnification of 15,000× or 20,000× to determine their surface areas as described above. The images of these particles are shown in FIGS. 7, 11, and 14. The membrane filter (including the particles) was then tilted at a 45° angle with respect to the image plane to expose an edge of each selected particle as shown in FIGS. 9, 10, 13 and 16. The width of the exposed edge of each selected particle was then measured using the calibrated line measurement feature in the software Fovea Pro 2.0 produced by Reindeer Graphics, Inc., (Asheville, N.C.). The measured width of each selected particle $T_m$ was then used to determine the calculated actual thickness T:

Since sine 45° =measured width ($T_m$)/calculated actual thickness ($T$)

therefore, the calculated actual thickness (T)=measured width ($T_m$)/sine 45° or $T=T_m/0.707106$.

The volume of each of the selected particles was then determined using the equation V=area (A)*calculated actual thickness (T) wherein area (A) is the surface area of the particle.

As the volume of an equivalent sphere can be calculated using the equation $V=(4/3)*\pi*R^3$, the radius of the equivalent sphere for each selected particle can be calculated using the equation $R=\sqrt[3]{(3/4)(1/\pi)(V)}$. The diameter (D) of the equivalent sphere for each selected particle is two times the radius, which is 2R. Table 2 lists the particle volume values and the associated equivalent sphere diameters for the three selected particles.

TABLE 2

Volumes and Equivalent Sphere Diameters of Selected Particles

| Particle Number | Volume V ($\mu m^3$) | Equivalent Sphere Diameter D ($\mu m$) |
|---|---|---|
| #1 | 14.8750 | 3.05 |
| #2 | 25.7018 | 3.66 |
| #3 | 4.1923 | 2.001 |

While specific embodiments have been illustrated and described, numerous modifications come to mind without departing from the spirit of the invention and the scope of protection is only limited by the scope of the accompanying claims.

What is claimed is:

1. A method for determining a particle size in a population of particles comprising the steps of:
   (i) positioning a particle on a flat surface;
   (ii) recording a digital image of the particle on the flat surface wherein the digital image is recorded with an image plane parallel to the flat surface and the digital image of the particle includes a digital background image of the flat surface;
   (iii) removing the digital background image of the flat surface to obtain an isolated digital image of the particle;
   (iv) determining a surface area (A) of the particle from the isolated digital image of the particle;
   (v) tilting the particle at a known angle (θ) with respect to the image plane to expose an edge of the particle;
   (vi) measuring a measured thickness ($T_m$) of the particle;
   (vii) determining a calculated actual thickness (T) of the particle by the equation $T=T_m/\sin\theta$;
   (viii) determining an equivalent sphere particle volume (V) of the particle by the equation V=A*T; and
   (ix) determining an equivalent spherical particle size diameter (D) of the particle by the equation $D=2*\sqrt[3]{(3/4)(1/\pi)(V)}$.

2. The method of claim 1, wherein the step of removing the digital background image of the surface is by applying one or more image analysis or image processing filters.

3. The method of claim 2, wherein the image analysis or image processing filter comprises the steps of:
 (i) removing the digital background image of the surface from the digital image of the particle by a number of pixels that also reduces the edges of the digital image of the particle by the same number of pixels;
 (ii) applying an image filter to remove the background, and,
 (iii) adding the same number of pixels back to the reduced edge of the digital image of the particle.

4. The method of claim 3, wherein said number of pixels is a whole number.

5. The method of claim 3, wherein said number of pixels is a fractional number.

6. The method of claim 1, which further comprises the steps of repeating the method with more than one particle on the surface to obtain an average value of the particle population size or a particle population size range.

7. The method of claim 1, wherein the step of positioning the particle on the surface comprises the steps of:
 (i) providing a dilute suspension of one or more particles in a liquid medium; and
 (ii) filtering the suspension onto a retention filter having a smooth flat surface.

8. The method of claim 7, wherein the particles are separated from each other on the filter.

9. The method of claim 7, wherein the filter is a 0.2 μm retention rated membrane filter and the particle has a particle size greater than 0.2 μm.

10. The method of claim 7, wherein the filter is an anodized aluminum membrane filter.

11. The method of claim 7, wherein the filter is a nuclear track-etched PC membrane filter.

12. The method of claim 7, wherein the suspension is an aqueous medium or a non-aqueous medium compatible with the membrane material.

13. The method of claim 1, wherein the size of the particle is less than 1 micron.

14. The method of claim 1, wherein the size of the particle is greater than about 350 nm.

15. The method of claim 1, wherein the size of the particle is from about 250 nm to about 350 nm.

16. The method of claim 1, wherein the size of the particle is greater than about 210 nm.

17. The method of claim 1, wherein the particle is crystalline.

18. The method of claim 1, wherein the particle is amorphous.

19. The method of claim 1, wherein the particle is an organic compound.

20. The method of claim 1, wherein the particle is an inorganic compound.

21. The method of claim 1, wherein the digital image is recorded with a scanning electron microscope, an optical microscope, a laser scanning microscope, a confocal microscope or a scanning probe microscope.

22. The method of claim 21, wherein the scanning electron microscope is a high resolution and a low voltage scanning electron microscope.

23. The method of claim 21, wherein the scanning electron microscope has a secondary electron detector.

24. The method of claim 21, wherein the scanning electron microscope has a backscattered detector.

25. The method of claim 21, wherein the scanning electron microscope has a multichannel plate detector.

26. The method of claim 1, wherein the known angle ($\theta$) of the particle is about 45 degrees.

27. The method of claim 1, wherein the step of measuring a measured thickness ($T_m$) comprises the steps of:
 (i) recording a digital image of the exposed edge of the tilted particle on the surface which includes digital background image of the surface; and
 (ii) measuring the width of the exposed edge of the particle from the recorded digital image of the tilted particle.

28. The method of claim 27, wherein the width of the edge of the particle is measured with a NIST traceable ruler.

29. The method of claim 27, wherein the width of the edge of the particle is measured by an image analysis software with a calibrated line measurement feature.

* * * * *